United States Patent [19]

Brossi et al.

[11] Patent Number: 5,310,935

[45] Date of Patent: May 10, 1994

[54] OPTICALLY ACTIVE 5-OXYGENATED (3S)-1,3-DIMETHYLOXINDOLE-3-ACETIC ACIDS

[75] Inventors: Arnold Brossi, Bethesda, Md.; Danilo C. Massari, Padova, Italy; Qian-Sheng Yu, Shanghi, China

[73] Assignee: Pharmagroup International, Baldwin, N.Y.

[21] Appl. No.: 906,508

[22] Filed: Jun. 30, 1992

[51] Int. Cl.$^5$ ............................................. C07D 209/34
[52] U.S. Cl. ................................................. 548/486
[58] Field of Search ........................................ 548/486

[56] References Cited

U.S. PATENT DOCUMENTS

| | | | |
|---|---|---|---|
| 3,462,450 | 8/1969 | Shen | 548/486 |
| 3,551,450 | 12/1970 | Frey et al. | 548/486 |
| 3,577,430 | 4/1971 | Plostnieks | 548/486 |
| 4,925,955 | 5/1990 | Asselin et al. | 548/432 |
| 5,206,261 | 4/1993 | Kawaguchi et al. | 548/486 |

FOREIGN PATENT DOCUMENTS 1158532 7/1969 United Kingdom .

OTHER PUBLICATIONS

Horne et al., J. Chem. Soc. Perkin Trans I, "Rapid Synthesis of Some Indole Alkaloids", pp. 3047–3051 (Dec. 1991).

Node et al., Chem. Lett., "A Chiral Total Synthesis of (-)-Physostigmine", pp. 57–60, (Jan. 1991).

Primary Examiner—Joseph P. Brust
Assistant Examiner—Mary Susan H. Gabilan
Attorney, Agent, or Firm—Roland Plottel

[57] ABSTRACT

The synthesis of optically active 5-oxygenated (3S)-1,3-dimethyloxindole-3-acetic acids R = H, $CH_3$, $C_2H_5$, $CH_2$—Ph

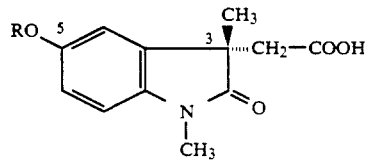

R = H, $CH_3$, $C_2H_5$, $CH_2$—Ph and their use in the synthesis of optically active (3aS-cis)-eseroline and (3aS-cis)-$N^1$-benzylnoreseroline, which are important intermediates in the synthesis of compounds related to (3aS-cis)-physostigmine and carbamate analogs, and of (3aS-cis)-$N^1$-benzylnor- and $N^1$-norphysostigmine and their carbamate analogs.

4 Claims, 1 Drawing Sheet

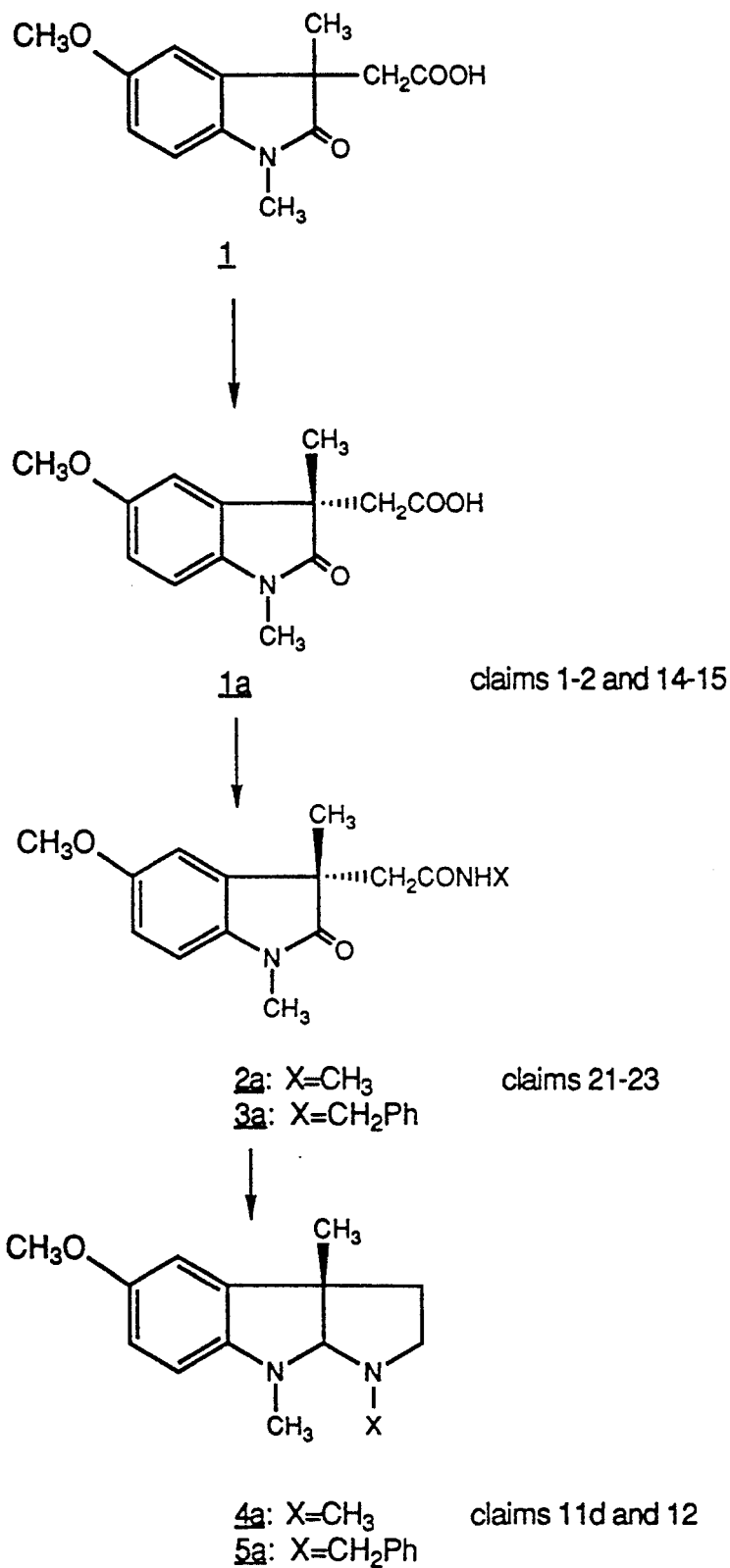

OPTICALLY ACTIVE 5-OXYGENATED (3S)-1,3-DIMETHYLOXINDOLE-3-ACETIC ACIDS

SUMMARY

The synthesis of opticall ative 5-oxygenated (3S)-1,3-dimethyloxindole-3-acetic acids,

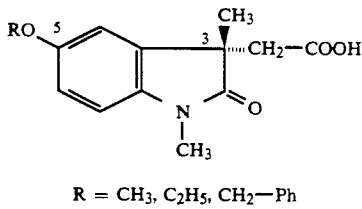

R = CH$_3$, C$_2$H$_5$, CH$_2$—Ph and their use in the synthesis of optically active (3aS-cis)-eseroline and (3aS-cis)-N$^1$-benzylnoreseroline, which are important intermediates in the synthesis of compounds related to (3aS-cis)-physostigmine and carbamate analogs, and of (3aS-cis)-N$^1$-benzylnor- and N$^1$-norphysostigmine and their carbamate analogs.

DRAWING

The drawing shows a synthetic scheme, in which underlined numbers identify particular substituents on the structural formulae. In the specification, those underlined numbers identify the corresponding entire compound. Non-underlined numbers in brackets identify a literature reference listed at the end of the specification.

STATE OF THE ART

Optically active (3aS-cis)-esermethole (DRAWING 8a, ethyl ether) has been obtained from Julian's oxindole 1 [1] by alkylation with chloroacetonitrile, reduction to the amine, cyclization to racemic esermethole and chemical resolution with camphorsulfonic acid and tartaric acid [2]. Chemical resolution of racemic esermethole with tartaric acid also was reported by Kobayashi [3], and by Dale and Robinson [4], who were unable to repeat Julian's resolution. The synthesis of unnatural (+)-esermethole required eight recrystallizations, to give optically pure material. Asymmetric alkylation of Julian's oxindole 1 with chloroacetonitrile in the presence of a chiral catalyst was reported [5] to afford the optically active nitrile 6a which was 73% optically pure (ee), and needed for further purification a reduction to the amine and its chemical resolution with dibenzoyltartaric acid. The optically pure amine was then reacted with methylchloroformate and the carbamate reduced to (3aS-cis)-esermethole (8a) with lithiumaluminum hydride [6].

Another route to optically active esermetholes was achieved by urea diastereomerization of racemic N$^1$-noresermethole (rac. 7), obtained from the nitrile mentioned above with sodium in ethanol [1] by reaction with optically active 1-phenylethylisocyanate, chromatographic separation of urea diastereomers and hydrolysis in high boiling alcohols [7, 8, 9]. This afforded (3aS-cis)-N$^1$-noresermethole 7a, which on reductive N-methylation afforded (3aS-cis)-esermethole 8a [10], and on N-benzylation (3aS-cis)-N$^1$-benzylnoresermethole 13a [9].

Conversion of methyl ether 8a (or ether analogs) into (3aS-cis)-eseroline 9a was accomplished with aluminum chloride [2,4], and with boron tribromide [8, 10]. (3aS-cis)-Eseroline 9a is required for the synthesis of natural physostigmine 10a and carbamate analogs. Use of (3aS-cis)-eseroline and its N$^1$-benzyl analog for making useful drugs is shown in reference [16].

Physostigmine which is medically used in Glaucoma, and shows good responses in Alzheimers patients when treated over an extended period of time, is being manufactured from plant material of African origin. There is need for a practical synthesis of this alkaloid, and of its carbamate analogs which have shown encouraging results in experimental animals for controlling the function of the enzyme cholinesterase.

There is a need to improve for a technical synthesis of 10a and carbamate analogs in the chemical resolution step, and this has now been accomplished with N-methyl-oxindoleacetic acid 4.

OBJECTS

It is an object of this invention to provide new optically active compounds of the (S)-configuration, useful as intermediates in the synthesis of natural physostigmine and analogs thereof.

Another object is to provide effective processes for obtaining such compounds in optically pure form.

Another object is to provide a method for the asymmetric synthesis of such compounds.

Yet another object is to provide a synthesis process for converting said (S)-configured optically active compounds to (3aS-cis)-eseroline or (3aS-cis)-N$^1$-benzylnoreseroline.

DETAILED DESCRIPTION OF THE INVENTION

The synthesis of the compounds described in this application is sketched in the Scheme (the DRAWING), and it requires the following chemical reactions.

Methylester 3 [11] was prepared from Julian's N-methyl-oxindole 1 [1] by O-methylation with dimethylsulfate in the presence of sodium hydroxide yielding the methyl ether 2, [12, 13], which on reaction with methyl bromoacetate gave the ester 3. This reaction also can be accomplished with esters of chloroacetic acid, such as methyl chloroacetate. Hydrolysis of 3 with aqueous-alcoholic sodium hydroxide afforded the acid 4 (94%).

The acid 4, on treatment with a stoichiometric amount of brucine-hydrate (Fluka Chemical Co.) in water, resulted in a brucine salt which was recrystallized from water to afford an optically pure material (40% yield). The brucine salt, when treated with aqueous sodium hydroxide, liberated the brucine, which can be removed and reused. The alkaline solution after acidification with hydrochloric acid and extraction with ethylacetate afforded the optically pure acid 5a of (S)-configuration (90%). The aqueous alkaline solution obtained after the filtration of brucine, contains largely the unnatural (+)-isomer of 5a with R-configuration, and it can be used to prepare the unnatural acid isomer.

Acid 5a, on treatment in pyridine solution with methanesulfonyl chloride, and exposure to ammonia gas, afforded on workup the oily nitrile 6a (90%) Reduction and cyclization of nitrile 6a with lithiumaluminum hydride in tetrahydrofuran, and usual workup, afforded on treatment with an ethanolic solution of fumaric acid the fumarate salt of N$^1$-noresermethole (7a) (89%). Reductive N-methylation of 7a in the presence of triethylamine gave (3aS-cis)-esermethole (8a) (89%) Treatment of methyl ether 8a with boron tribromide in dichloromethane solution afforded (3aS-cis)-eseroline (9a) (85%).

The chemical reactions can equally well be carried out with ethyl ether and benzyl ether analogs of acid 5a.

Acid 5a on reaction with thionyl chloride to form the acid chloride, and followed by treatment with methylamine afforded the methylamide 11a. This optically pure amide on reduction with lithium aluminum hydride in tetrahydrofuran afforded the (3aS-cis)esermethole (8a) directly and in almost quantitative yield. Similarly, reaction of the acid chloride with benzylamine forms the benzyl amide 12a, which on reduction with LAH affords the (13aS-cis)-$N^1$-benzylnoreseroline methyl ether 13a. Amides of acid 5a and its ether analogs also can be obtained by reacting the acid with alkyl- or benzyl- or arylisocyanates in an appropriate solvent such as toluene in the presence of a tertiary amine such as triethylamine. Another method of preparing these amides involves heating the acid 5a or its ether analogs along with the amide-forming reactant in high boiling solvents, such as xylene, with the azeotropic removal of water The conversion of amides of 5a into esermethole, or its $N^1$-substituted analogs, also can be accomplished by reduction with sodium in alcohols, or by using diisobutylaluminum hydride=DIBAH as a reducing agent instead of LAH.

It has been reported that N-benzylation of 7a afforded the (3aS-cis)-$N^1$-benzylnoresermethole 13a [9] and on O-demethylation (3aS-cis)-$N^1$-benzylnoreseroline required for the synthesis of norphysostigmine and carbamate analogs This also can be accomplished from the acid 5a by procedures given above via compounds 12a and 13a.

For the recrystallization of the brucine salt, water alone is an excellent and preferred solvent. Aqueous solvents in general can be used, such as water, and mixtures of water with lower alcohols or acetone Although brucine has been shown to be an excellent resolving agent of acid 4, there is good reason to believe that this also could be accomplished with other alkaloids, such as quinidine, cinchonine, etc., or with synthetic amines such as 1-phenyl-ethylamines or dehydroabietylamine.

The overall yield for converting the readily available oxindole 1 into optically pure (3aS-cis)eseroline 9a is 23%, and it compares well with the best yields obtained in other syntheses of 9a. The compounds are easy to purify, the chemical resolutions are carried out in water, and the resolving agent can be recovered, which makes this process attractive for a technical synthesis.

To even further improve on the present synthesis of the optically active (3S)-acid 5a we have carried out the chiral phase-transfer alkylation of N-methyl-oxindole methyl ether 2 with methyl bromoacetate in the presence of the commercially available N-[4-trifluoromethylbenzyl]cinchoninium bromide (Fluka) to afford after hydrolysis of the ester the acid 5a which was 70% enriched in the (S)-enantiomer. Optically pure material can be obtained from this acid by a chemical purification with brucine, as described for the optical resolution of 4, but affording a much higher overall yield of 5a. Optically pure acid 5a can also be obtained from the 70% enriched acid by crystallization from ethylacetate or water. Asymmetric alkylation of the N-methyloxindole ether 2 also can be achieved with other alkyl haloacetates, such as ethyl or methyl chloroacetate. Other quaternary Cinchona alkaloids, such as benzylcinchoninium bromide also can be used. Asymmetric alkylations have been described in the literature [5][14][15].

EXAMPLES

Variations in the particular procedures, conditions and proportions of materials used in the following Experiments can be employed without departing from the invention.

Experiment 1

N-Methyloxindole 1 (36.8 g) was dissolved in 5% aqueous KOH (250 ml), and dimethyl sulfate (30 ml) added under stirring. After addition the reaction mixture was heated to 90 degrees C for 1 h. After cooling to room temperature the reaction product was extracted with ethylacetate, the extract washed with water, dried (MgSO4), and the solvent evaporated. Crystallization of the residue from hexane afforded methyl ether 2 (36, 2 g,94%) of m.p. 87°–88° degrees C. which was TLC pure (silica gel, CH2C'2 with 10% MeOH).

Experiment 2:

Methyl ether 2 (6 g) was dissolved in a methanolic solution of sodium methoxide (45 ml), prepared by dissolving sodium (1.86 g) in methanol (45 ml), methyl bromoacetate (7.95 ml) was added, and the reaction mixture refluxed for 2 h. After evaporation of solvent the residue was partitioned between water and ethyl acetate, washed with water, aqueous 1N HCl, and brine. The residue obtained after the evaporation of the solvent was crystallized from ethylacetate and petroleum ether, to afford 1,3-dimethyl-5-methoxyoxindol-3-acetic acid methyl ester 3 of m.p. 83°–84° degrees C. (6.3 g, 76%).

Experiment 3

Methyl ester 3 (8 g) was dissolved in methanol (200 ml) containing sodium hydroxide (10 g), and the reaction mixture was stirred at r.t. (room temperature) for 2 h. The solvent was evaporated, the residue rendered acidic with 3N HCl, then extracted with ethyl acetate, the extract dried (MgSO4) and evaporated, to give colorless crystals of 1,3-dimethyl-5-methoxyoxindole-3-acetic acid (4, 7.1 g, 94%) of m.p. 120°–121° degrees C.

Experiment 4

Acid 4 (7.1 g) and brucine hydrate (13.3 g) were dissolved in water (150 ml) under cautious warming. The clear solution was left standing for 12 h. at room temperature and the brucine salt filtered, and crystallized twice from water, to afford optically pure brucine salt of 5a (10.8 g): m.p. 115° degrees C.; [α]D −33.2 degrees (c=1.0, EtOH); $C_{36}H_{42}N_3O_8$·4 $H_2O$: calc. C 60.34, H 6.98, N 5.87%; found C 60.59, H 6.81, N 5.87%. The brucine salt obtained above was dissolved in water (200 ml) under warming, 5N sodium hydroxide solution added (30 ml) and the brucine which precipitated removed by filtration. The brucine can be crystallized from acetone-water to afford material which is optically pure and can be reused. The filtrate was acidified with 2N hydrochloric acid and acid 5a extracted with ethylacetate, to afford after washing the extract with brine, drying (MgSO4) and concentration the optically pure acid 5a as colorless crystals (3.5 g) : m.p. 124°–125° degrees C.; [α])D= −48.7° degrees (C.=0.96,CHCl3). The material is on TLC identical with racemic 4 (silica gel, $CH_2Cl_2$ with 1% MeOH).

Experiment 5

Acid 5a (2.5 g) was dissolved in dry pyridine (50 ml) and cooled to 0° degrees C., and added dropwise with methanesulfonyl chloride (1.2 g). After 1 h. dry ammonia gas was passed through the solution for 5 min., and excess ammonia removed in the vacuum for 5 min. The solution was cooled to 0° degrees C. and added with methanesulfonyl chloride (1.2 g) and stirred for 24 h. at r.t. The reaction mixture was then poured into 2N HCl under cooling and the pH adjusted to 7.0. Extraction with ethylacetate, washing with brine, drying ($MgSO_4$) and removal of solvent afforded nitrile 6a as a yellowish oil (2.2 g, 95%) : $[\alpha]D+57.5°$ degrees (C.=0.5, $CHCl^3$); ir frequencies at 2230, 1730, 1710, 1690 and 1600 $cm^{-1}$; MS (EI) m/z 230 (M+), 215 (M+ −$CH_3$), 190 (M+ −$CH_2CN$).

Experiment 6

Nitrile 6a (784 mg) was dissolved in THF (60 ml) and added with lithiumaluminum hydride (600 mg). After stirring for 1 h. at r.t. the reaction mixture was refluxed for 10 min., the solvent evaporated and the residue dissolved in 2N HCl. The aqueous solution was washed with ether, then rendered alkaline with $NaHCO_3$, extracted with ether, dried ($MgSO_4$), and concentrated in vacuum to 10 ml. The ether concentrate was added with a saturated alcoholic solution of fumaric acid (500 mg) to afford on standing the fumarate salt of (3aS-cis)-$N^1$-noresermethole (7a, 980 mg, 89%) : m.p. 199°–200° degrees C.; $[\alpha]D−73°$ degrees (C.=0.7, MeOH); TLC identical with a standard sample (silica gel, $CH_2Cl_2$ with 5% MeOH).

Experiment 7

Free base 7a was prepared from the fumarate salt described in Experiment 6 by treating its aqueous solution with 10% aqueous $NaHCO_3$ and extraction with ether. The free base 7a (500 mg) was dissolved in MeOH (1 ml), added with triethylamine (0.7 ml), and 37% aqueous formaldehyde (1 ml), stirred for 1 h. and added with $NaBH_4$ (300 mg). After 1 h. the reaction mixture was concentrated in vacuo, acidified with 2N HCl, washed with ether, basified with an aqueous solution of $Na_2CO_3$, and extracted with ether. The ether solution after passing through a short column of silica gel (1 g), yielded after evaporation of solvent TLC-pure (3aS-cis)-esermethole 8a as an oil : $[\alpha]D−88.2°$ degrees (C.=1.2, $CHCl_3$).

Experiment 8

Esermethole 8a (388 mg) in $CH_2Cl_2$ (10 ml) was added dropwise with a solution of $BBr_3$ (1 ml in 10 ml $CH_2Cl_2$) under stirring, and stirring continued for 2 h. under nitrogen. After evaporation of solvent the residue was dissolved in MEOH (10 ml), and stirred for 1 h. Evaporation of solvent gave a residue which was dissolved in $H_2O$ (20 ml), basified with aqueous $NaHCO_3$, and extracted with ether. The ether extract was dried ($MgSO_4$) and concentrated in vacuo to give on standing at 0° degrees C. for 24 h. (3aS-cis)-eseroline (9a, 225 mg) : m.p. 125°-126° degrees C.; $[\alpha]D−112°$ degrees (C.=0.4, MeOH).

Experiment 9

Free base 7a, prepared from its fumarate salt (2 g) by the procedure detailed in Experiment 7, was dissolved in $CH_3CN$ (30 ml), added with dry $K_2CO_3$ (50 mg) and benzylbromide (2 g), and the reaction mixture stirred at r.t. for 1 h. After evaporation of solvent the residue was taken up in $CH_2Cl_2$ containing 1% MeOH and filtered through a short silical gel column, to afford the $N^1$-benzyl analog of 8a (1.3 g, oil) : CIMS 309 (M+ +1); $[\alpha]D−51.4°$ degrees (C.=1,5, $CHCl_3$); TLC pure (silica gel, $CH_2Cl_2$ with 1% MeOH).

Experiment 10

$N^1$-Benzylnoresermethole described in Experiment 9 (1.3 g) was dissolved in $CH_2Cl_2$ (20 ml), and added with a solution of $BBr_3$ in $CH_2Cl_2$ (1M, 20 ml) under stirring. After 1 h. the solvent was evaporated and the residue dissolved in MeOH (20 ml), and left for 1 h. After evaporation of solvent, addition of $H_2O$ (20 ml), and basification with aqueous $NaHCO_3$ the material was extracted with ether. The ether extract, after washing it with brine, drying ($MgSO_4$), and evaporation of solvent yielded $N^1$-benzylnoreseroline ($N^1$-benzyl analog of 9a, 1.2 g) as an oil : CIMS m/z 295 (M+ +1); $[\alpha]D−60.2°$ degrees (C.=1, $CHCl_3$).

Experiment 11

To N-methyloxindole 2 (955 mg) and N-[4-trifluoromethyl-benzyl)cinchoninium bromide (Fluka, 267 mg) which were added to benzene (120 ml) was added 50% aqueous KOH (20 ml) under stirring in a nitrogen atmosphere. After 20 min. bromoacetic acid methyl ester (1530 mg) was added dropwise over a period of 1 h. at 10° degrees C., and the reaction mixture kept for another 1.5 h. After addition of water (50 ml) the reaction mixture was extracted with ether (3×50 ml), the etherial extracts washed with 1.5% HCl, brine and then dried over $Na_2SO_4$. After evaporation of solvent the residue was flash-chromatographed over silica gel ($CH_2Cl_2$/EtOAc) to give the optically enriched ester 3 (986 mg) : $[\alpha]D=−10°$ degrees (C.=0.5, EtOH). The spectral data are identical with those of racemic 3.

Experiment 12

The methyl ester prepared in Experiment 11 was hydrolyzed as described in Experiment 3, to yield the optically enriched acid 5a: m.p. 120° degrees C.; $[\alpha]D=−25°$ degrees (C.=0.5, $CHCl_3$). The enantiomeric excess was by chiral HPLC analysis of the methyl ester prepared with etherial diazomethane shown to contain 70% of the acid 5a of (S)-configuration.

Experiment 13

1769 mg (7.1 mmol) of compound 5a as prepared in Experiment 12 and brucine tetrahydrate (3312 mg, 7.1 mmol) were dissolved in 40 ml distilled water, warming cautiously till clear. The solution was allowed to stand at r.t.; the brucine salt crystallized at once. The collected crystals were recrystallized at the same conditions two times to get the brucine salt of 5a, 2729 mg (3.8 mmol); m.p. 115° degrees C., $[\alpha]D−33.2°$ degrees (C.=1.0, ETOH). Using the same procedure followed in Experiment 4, there was obtained as crystals optically pure 5a: 884 mg (3.67 mmol) (5 to 7%), m.p. 124°–125° degrees C., $[\alpha]D−48.7°$ degrees (c=1.0, $CHCl^3$.

Experiment 14

Compound 5a is useful as a starting material in syntheses of optically active Calabar alkaloids. This experiment illustrates one step in such a synthesis.

266 mg (1.07 mmol) of compound 5a and 221.5 mg (1.61 mmol) of anhydrous $K_2CO_3$ were added into 15 ml of acetone, then 2 g of CH3I was added. The reaction mixture was stirred overnight at r.t. under N2. After evaporation of solvent, the residue was partitioned between Et2O and H2O. The organic layer was washed by brine, then dried over Na2SO4. After evaporation of solvent, the residue was dissolved in 6 ml of THF, and 48 mg (1.26 mmol) of LiAlH4 was added in portions. The mixture was stirred under N2 for 1 h. The solvent was evaporated and residue was partitioned between 1.5% aqueous HCL and Et2O. The organic layer was washed with brine, dried over Na2SO4 and evaporated to give (−)-physovenol methyl ether as oil 199 mg (85%). TLC and MS are correct. $[\alpha]D = -81.2°$ degrees (c=0.6, EtOH). The structural formula of (−)-physovenol methyl ether is:

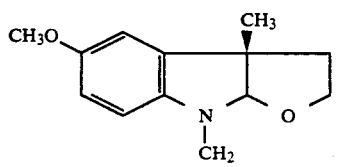

Experiment 15

In a sealed tube was added compound 5a (230 mg, 0.92 mMol), methylisocyanate (114 mg; 2mMol) and triethylamine (5 mg) in dry toluene (2 ml). The sealed tube was heated by oil bath and the reaction mixture was stirred by a magnetic stirrer for 2.5 h, meanwhile the temperature of oil bath was kept at about 7° degrees C. Then the tube was opened, the mixture was stirred for another 1 h. and the temperature of oil was kept at 90° degrees C. at the same time. After evaporation of solvent the residue was dissolved by CHCl3 (2.5 ml), washed by 1N NaOH (0.5 ml) and brine, dried by MgSO4 Evaporation of CHCl3 gave crude product which was recrystallized from hexane to give the methylamide 11a as crystals (169 mg., 70%) : mp 148°-149° degrees C.; $[\alpha]D - 29.6°$ degrees (c.=0.5, CHCl3); MS(EI), m/z 262=(M+); 1H NMR CDCl3: J1.35 (S, 3H, CH3), 2.60-2.80 (m, 2H, −CH2—CO), 2.85 ( S, 3H, HN-CH3), 3.17 (S, N-CH3), 3.76 (S, 3H, —O—CH3), 6.70 6.90 (m, 3H, Ar-H). Anal. calcd. for $C_{14}H_{18}O_3N_2$—C 38.13; H6.91, N 10.68. Found—C 38.10, H 7.10; N 10.51.

Experiment 16

The benzylamide 12a was prepared as described in Experiment 15, using benzylisocyanate instead of methylisocyanate. Compound 12a was obtained as crystals (80.2%) mp. 104°-105° degrees C.; $[\alpha]D = -48.9°$ degrees (c=1.0, CHCl3); MS(EI) m/z 338 (M+); 1H NMR (CDCl3)=J 1.20 (S.3H, —CH3), 2.60-2.90 (m, 2H, —CH2CO—), 3.09 (S, 3H, NCH3), 3.80 (S, 3H, —OCH3), 4.20-4.50 (2H, m. Ph-CH2), 6.50-7.50 (m, 8H, Ar-H). Anal. Cald. for $C_{20}H_{22}O_3N_3$=C 70.98; H 6.55; N 8.28. Found=C 70.90; H 6.70; N 8.14.

Experiment 17

LiAlH4 (72 mg) was added into THF (2 ml). The mixture was heated by an oil bath and kept refluxing, stirring under N2. The methyamide 11a (160 mg, 0.61 mMol) in THF (1 ml) was added dropwise into the above reflux mixture during 0.5 h. After stirring for 1 h. at reflux the reaction mixture was cooled to room temperature, then saturated brine was added dropwise until no more H2 evolution was evident. The THF solution was filtered to remove the solid and then solvent was evaporated. The residue (its TLC showed 2 spots) was chromatographed on silica gel (CH2Cl2/MeOH, 100:1) to get less polar major product as a gum which was added to a saturated alcoholic solution of fumaric acid (7.9 mg) and left overnight in the refrigerator to give the fumaric salt of (−)-O-Methyleseroline 8a (127 mg, 60%); mp 135°-136° C.; $[\alpha]D = -98°$ degrees (c=1, MeOH); MS and 1H-NMR are identical with (+)-O-Methyleseroline [17].

Experiment 18

(−)-N1-Benzyl-O-methylnoreseroline 13a was similarly prepared as described for the preparation of 8a. Chromatography gave less polar major product 13a as an oil (65%), $[\alpha]D - 50.1°$ degrees (C.=1, CHCl3), MS and 1H-NMR are identical with known compound [18].

REFERENCES

[1] P. L. Julian and J. Pikl, *J. Am. Chem. Soc.* 1935, 57, 563.
[2] P. L. Julian and J. Pikl, *J. Am. Chem. Soc.* 1935, 57, 755.
[3] T. Kobayashi, *Liebigs Ann. Chem.* 1938, 536, 143.
[4] F. J. Dale and B. Robinson, *J. Pharm. Pharmacol.* 1970, 22, 889.
[5] T. B. K. Lee and G. S. K. Wong, *J. Org. Chem.*, 1991, 56, 872.
[6] Q. S. Yu and A. Brossi, *Heterocycles*, 1988, 27, 1709.
[7] B. Schonenberger and A. Brossi, *Helv. Chim. Acta* 1986, 69, 1486.
[8] Q. S. Yu and A. Brossi, *Heterocycles* 1988, 27, 745.
[9] Q. S. Yu, J. R. Atack, S. I. Rapoport, and A. Brossi, *J. Med. Chem.* 1988, 31, 2297.
[10] B. Schonenberger, A. E. Jacobson, A. Brossi, R. Streaty, W. A. Klee, J. L. Flippen-Anderson, and R. Gilardi, *J. Med. Chem.* 1986, 29, 2268.
[11] Y. Luo, Q. S. Yu, L. Chrisey, and A. Brossi, *Heterocycles*, 1990, 31, 283.
[12] C. Wright, M. Shulkind, K. Jones, and M. Thompson, *Tetrahedron Lett.* 1987, 28, 6389.
[13] R. Underwood, K. Prasad, O. Repic, and G. H. Hardtmann, *Synthetic Communications* 1992, 22, 343.
[14] U. H. Dolling, P. Davis, and E. J. J. Grabowski, *J. Am. Chem. Soc.* 1984, 106, 446.
[15] D. L. Hughes, U. H. Dolling, K. M. Ryan, E. F. Schoenewaldt, E. J. J. Grabowski, *J. Org. Chem.* 1987, 52, 4745.
[16] A. Brossi, *Med. Res. Reviews* 1992, 12, 1–26.
[17] Q. S. Yu and A. Brossi *Heterocycles* 1988, 27, 747.
[18] Q. S. Yu, J. R. Atack S. I. Rapoport and A. Brossi *J. Med. Chem.* 1988, 31, 2299.

We claim:

1. An optically pure (3S) configured compound of the formula

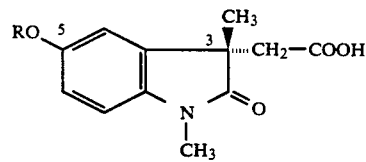

wherein R is CH3, C2H5 or CH2-Ph.

2. A compound according to claim 1 wherein R is methyl.

3. A compound according to claim 1 wherein R is ethyl.

4. A compound according to claim 1 wherein R is benzyl.

* * * * *